(12) United States Patent
Urbanski et al.

(10) Patent No.: US 10,864,041 B2
(45) Date of Patent: Dec. 15, 2020

(54) SIDE-PORT CATHETER

(71) Applicant: Baylis Medical Company Inc., Montreal (CA)

(72) Inventors: John Paul Urbanski, Toronto (CA); Hans Fischer, Toronto (CA); Yun Uhm, Toronto (CA)

(73) Assignee: Baylis Medical Company Inc., Mississauga (CA)

( * ) Notice: Subject to any disclaimer, the term of this patent is extended or adjusted under 35 U.S.C. 154(b) by 628 days.

(21) Appl. No.: 15/115,514

(22) PCT Filed: Jan. 29, 2015

(86) PCT No.: PCT/IB2015/050682
§ 371 (c)(1),
(2) Date: Jul. 29, 2016

(87) PCT Pub. No.: WO2015/114560
PCT Pub. Date: Aug. 6, 2015

(65) Prior Publication Data
US 2017/0172653 A1    Jun. 22, 2017

Related U.S. Application Data

(60) Provisional application No. 61/932,891, filed on Jan. 29, 2014.

(51) Int. Cl.
*A61B 18/14* (2006.01)
*A61B 17/3207* (2006.01)
(Continued)

(52) U.S. Cl.
CPC ...... *A61B 18/1492* (2013.01); *A61B 17/3207* (2013.01); *A61B 17/34* (2013.01);
(Continued)

(58) Field of Classification Search
CPC ........ A61B 17/320068; A61B 17/3207; A61B 17/34; A61B 18/1477; A61B 18/1492;
(Continued)

(56) References Cited

U.S. PATENT DOCUMENTS

| 2,116,083 A | 5/1938 | Rusch |
| 5,342,303 A | 8/1994 | Ghaerzadeh |

(Continued)

FOREIGN PATENT DOCUMENTS

| EP | 2574364 A1 | 4/2013 |
| WO | 2012009187 A1 | 1/2012 |

OTHER PUBLICATIONS

European Patent Office Supplementary Search Report, dated Aug. 29, 2017.
(Continued)

*Primary Examiner* — Thomas A Giuliani
*Assistant Examiner* — Christine A Dedoulis
(74) *Attorney, Agent, or Firm* — Glenn Arnold; Vincent Man; Samuel Tekie

(57) ABSTRACT

Methods and apparatus are disclosed for a catheter having a side-port, through which a device, for example, a wire, may be advanced, and a vestibule in the outer surface of the catheter at the distal edge of the side-port. The vestibule is operable for providing a gap between the catheter body and a distal tip of the device positioned through the side-port whereby the vestibule facilitates advancement of the device 5 through the side-port and through tissue towards a desired trajectory. In examples wherein the device is a wire having a distal tip electrode, energy may be delivered to a tissue adjacent the side-port, while avoiding damage to a wall of the catheter body.

17 Claims, 8 Drawing Sheets

(51) Int. Cl.
*A61B 17/34* (2006.01)
*A61B 18/18* (2006.01)
*A61M 25/00* (2006.01)
A61B 17/22 (2006.01)
A61B 90/00 (2016.01)
A61B 18/00 (2006.01)

(52) U.S. Cl.
CPC ....... *A61B 18/1815* (2013.01); *A61M 25/007* (2013.01); *A61B 18/1477* (2013.01); *A61B 2017/22044* (2013.01); *A61B 2017/22095* (2013.01); *A61B 2018/00601* (2013.01); *A61B 2090/3966* (2016.02)

(58) Field of Classification Search
CPC ...... A61B 18/1815; A61B 2017/22044; A61B 2017/22095; A61B 2017/00601; A61B 2090/3966; A61B 18/1485; A61B 18/148; A61B 17/3421; A61B 2018/1465; A61B 2018/1475; A61M 25/007; A61M 25/0079; A61M 25/0074
USPC .......................................................... 606/45
See application file for complete search history.

(56) References Cited

U.S. PATENT DOCUMENTS

| | | | |
|---|---|---|---|
| 5,628,770 A | 5/1997 | Thome et al. | |
| 5,697,281 A * | 12/1997 | Eggers | A61B 18/12 604/114 |
| 6,217,527 B1 * | 4/2001 | Selmon | A61B 17/3207 600/585 |
| 6,221,049 B1 | 4/2001 | Selmon et al. | |
| 7,004,173 B2 | 2/2006 | Sparks et al. | |
| 7,833,215 B2 | 11/2010 | Appling | |
| 7,840,261 B2 | 11/2010 | Rosenman | |
| 7,896,888 B2 | 3/2011 | Osborne et al. | |
| 8,374,680 B2 * | 2/2013 | Thompson | A61B 17/3207 600/424 |
| 9,301,774 B2 * | 4/2016 | O'Day | A61B 17/3207 |
| 2003/0032936 A1 | 2/2003 | Lederman | |
| 2006/0030864 A1 | 2/2006 | Kennedy, II et al. | |
| 2006/0094930 A1 | 5/2006 | Sparks et al. | |
| 2006/0106338 A1 * | 5/2006 | Chang | A61M 25/0084 604/104 |
| 2006/0276749 A1 * | 12/2006 | Selmon | A61B 6/12 604/164.01 |
| 2007/0197256 A1 | 8/2007 | Gellman et al. | |
| 2007/0203486 A1 * | 8/2007 | Young | A61B 18/148 606/41 |
| 2008/0045924 A1 * | 2/2008 | Cox | A61B 10/0045 604/515 |
| 2008/0103504 A1 * | 5/2008 | Schmitz | A61B 17/32001 606/79 |
| 2008/0208187 A1 * | 8/2008 | Bhushan | A61B 18/1206 606/41 |
| 2013/0310767 A1 | 11/2011 | Solar et al. | |
| 2013/0085477 A1 * | 4/2013 | Deshpande | A61M 1/3653 604/523 |
| 2013/0090674 A1 | 4/2013 | Escudero et al. | |
| 2013/0158507 A1 * | 6/2013 | Brown | A61M 25/007 604/506 |
| 2013/0303897 A1 | 11/2013 | Pursley | |
| 2014/0142607 A1 * | 5/2014 | Cage | A61M 25/0054 606/185 |
| 2014/0371718 A1 * | 12/2014 | Alvarez | A61M 25/0074 604/510 |

OTHER PUBLICATIONS

Patent Corporation Treaty, International Search Report and Written Opinion of the International Searching Authority for International Application No. PCT/IB2015/050682 dated Jun. 3, 2015.

* cited by examiner

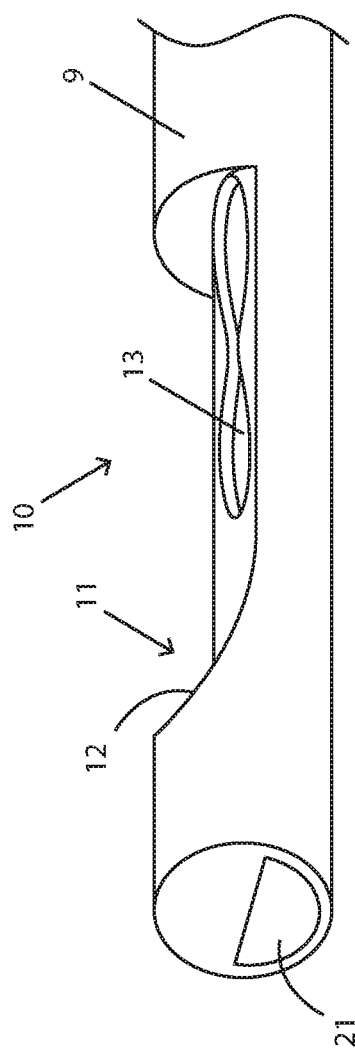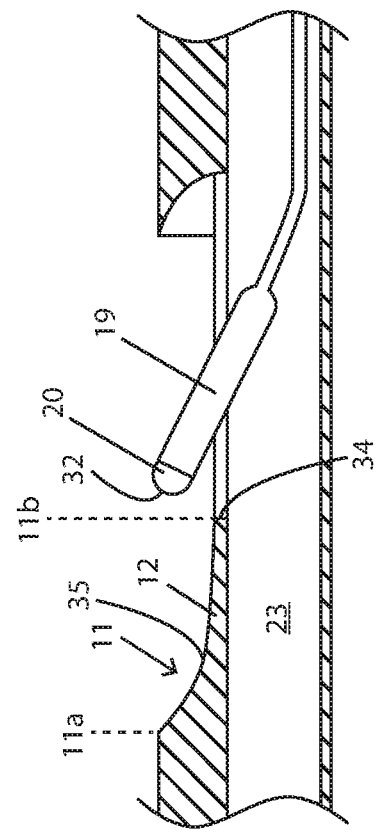

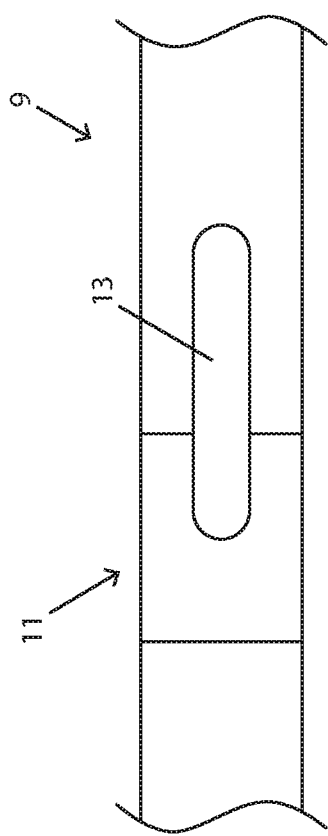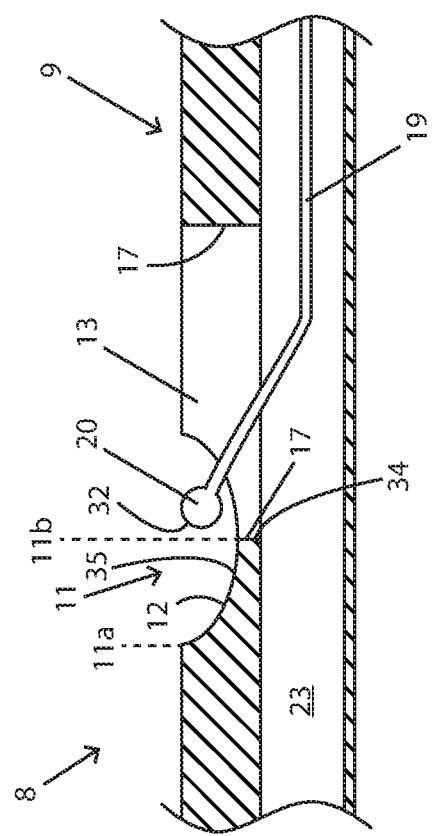

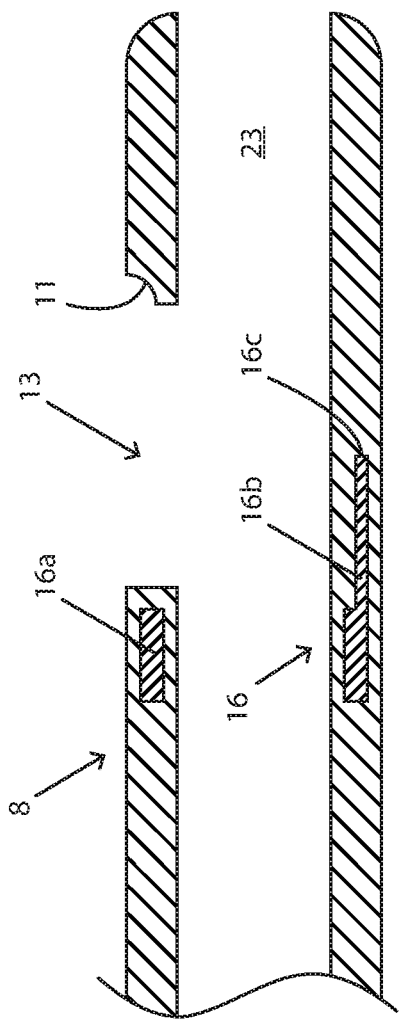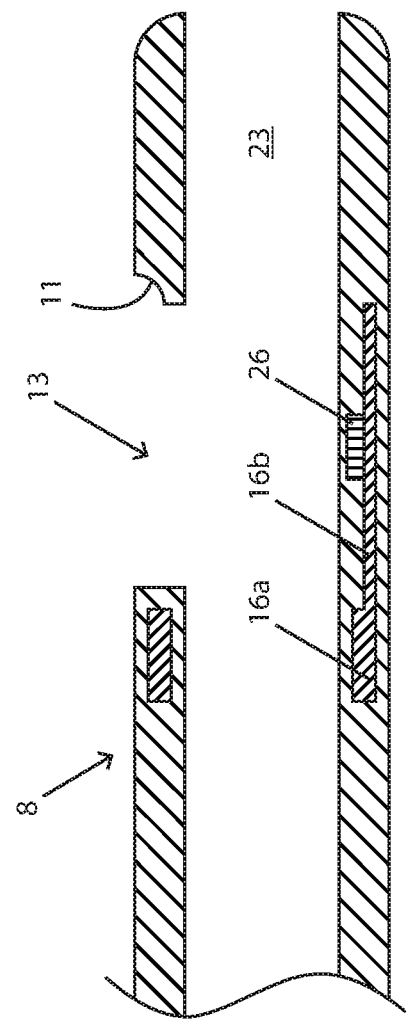

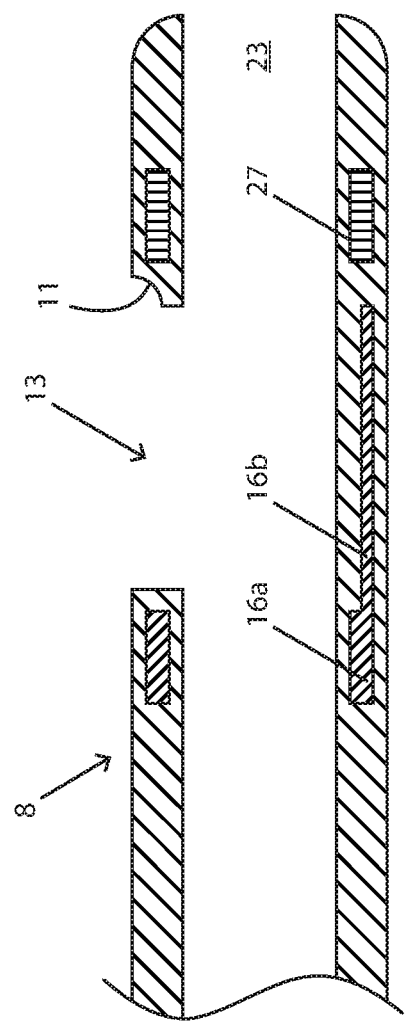

SIDE-PORT CATHETER

CROSS-REFERENCES TO RELATED APPLICATIONS

This application claims the benefit of the filing date of U.S. Provisional Application Ser. No. 61/932,891, filed Jan. 29, 2014, entitled "Side-port Catheter", the entire disclosure which is hereby incorporated by reference into the present disclosure. This application also incorporates by reference the entire disclosure of PCT International Application Ser. No. PCT/IB2015/050396, filed Jan. 19, 2015, entitled "Collapsible Tip Re-entry Catheter".

TECHNICAL FIELD

The disclosure relates to the field of medical devices, and in particular relates to the field of catheters.

SUMMARY

Enabling a medical device (e.g. a wire such as an angled wire) to be directed through a catheter side-port in a desired direction, such that damage to the catheter is avoided, is achieved by providing a side-port catheter having a geometry, including, for example, a vestibule at or about the distal end of the side-port, which facilitates advancement of the tip of the wire through the side-port in a desired trajectory while avoiding contact with the catheter body. Some embodiments of the wire (or other device) include an electrode at the distal tip for delivering energy to tissue adjacent the catheter without damaging the catheter.

In one broad aspect, embodiments of the present invention are for a catheter comprising: a catheter body, the catheter body comprising a catheter body wall defining a lumen, and a side-port defined by a side of the catheter body wall in fluid communication with the lumen, a first region of the catheter body wall at or adjacent to a distal end of the side-port being oriented in a first direction, and a second region of the catheter body wall adjacent to the first region being oriented in a second direction.

As a feature of this broad aspect, some embodiments include the first and second regions cooperating to provide a longitudinal gap between a distal wall of the side-port and an outer surface of the catheter body.

In a further broad aspect, embodiments of the present invention include a method of using a medical device for re-entry into a true lumen of a vessel, the method comprising the steps of: (a) advancing the medical device through a lumen of a catheter positioned within a wall of the vessel; (b) locating a side-port of the catheter; and (c) positioning a distal tip of the medical device through the side-port such that the distal tip contacts a tissue of the wall of the vessel substantially without contacting a body of the catheter.

In another broad aspect, embodiments of the present invention include a method of using a medical for re-entry into a true lumen of a vessel, the method comprising the steps of (a) advancing a medical device through a lumen of a catheter positioned within a wall of the vessel; (b) locating a side-port of the catheter; and (c) positioning the medical device through the side-port such that a distal tip of the medical device is distanced from both a body of the catheter as well as a tissue of the vessel.

In another broad aspect, embodiments of the present invention include a catheter for use with an angled wire for re-entry into a true lumen of a vessel, the catheter comprising: a catheter body, the catheter body comprising a catheter body wall defining an off-centre lumen and a side-port in fluid communication with the lumen, a thickness of the catheter body wall about the side-port and a length of the side-port configured such that, in use, a tip of the angled wire positioned through the side-port in a relaxed state is in contact with a tissue of the vessel substantially without contacting the catheter body wall.

In a further broad aspect, embodiments of the present invention include a kit comprising a catheter for use with an angled wire for re-entry into a true lumen of a vessel and at least one angled wire.

In a further broad aspect, embodiments of the present invention are for a system comprising a catheter for use with an angled wire for re-entry into a true lumen of a vessel, at least one angled wire, and an electrosurgical generator for delivering electrical energy to the at least one angled wire.

BRIEF DESCRIPTION OF THE DRAWINGS

In order that the invention may be readily understood, embodiments of the invention are illustrated by way of examples in the accompanying drawings, in which:

FIG. 2b is a top view of a portion of a catheter which includes an alternative side-port embodiment;

FIG. 2c is a top view of a portion of a catheter which includes another alternative side-port embodiment;

FIG. 3a is a perspective view of another embodiment of a catheter including a side-port;

FIG. 3b is a cut away side view of the catheter of FIG. 3a;

FIG. 4a is a top view of another embodiment of a catheter including a side-port;

FIG. 4b is a cut away side view of the catheter of FIG. 4a;

FIGS. 5a to 5c are cut away views showing different embodiments of markers; and

DETAILED DESCRIPTION

Figure 1:
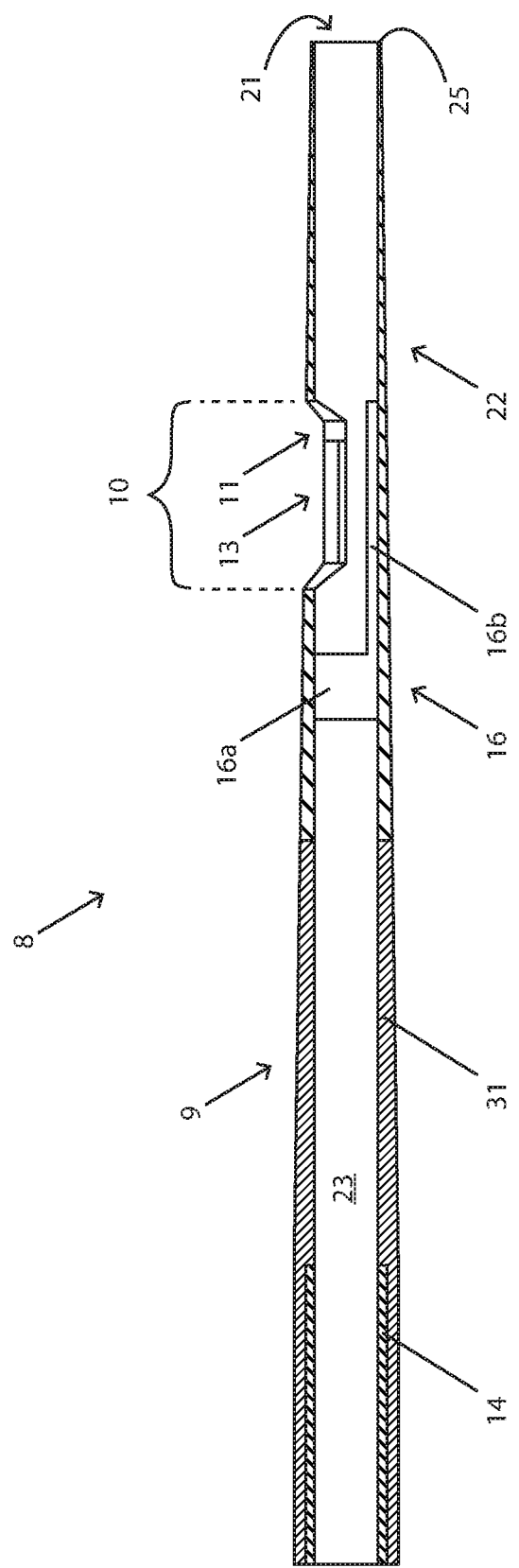
FIG. 1 is a cut away side view of an embodiment of a catheter.

Some surgical procedures include a wire being advanced through a vessel of a patient's body and taking a sub-intimal path, intentionally or unintentionally. A physician then has the option of using a device such as a re-entry catheter with a side-port to regain access to the true lumen (i.e. the lumen of the vessel). For example, a wire may be directed through a passive side-port (i.e. the side-port of a non-deflecting catheter) of the re-entry catheter to create a channel back to the true lumen. Once access to a true lumen of a vessel has been regained, a wire advanced into the true lumen may be used as a rail to advance devices, such as balloons or stents, into the true lumen.

To re-enter a true lumen, a guide-wire (or any other suitable device) typically changes trajectory from sub-intimal advancement parallel with the longitudinal axis of the vessel lumen, to a trajectory oblique or normal to the longitudinal axis of the vessel lumen, generally directed towards the center of the vessel lumen. Typical side-port re-entry catheters have a side-port wherein the distal surface of the side-port substantially comprises a single surface which may be curved or planar (i.e. flat). When exiting the catheter through the side-port, the tip of a device will slide along the distal surface of the side-port. When a typical re-entry catheter is positioned sub-intimally, tissue of the vessel wall is typically pressed/biased against the side-port of the catheter obstructing advancement therethrough, thereby constraining a tip of a wire which has been advanced long the single surface of the side-port distal side, whereby the tip of the wire will simultaneously press against and contact the distal surface of the side-port and the tissue. Upon delivery of energy (e.g. mechanical, electrical, optical, ultrasonic, and etc.) to the wire tip positioned at the side-port, rather than advancing the wire through the tissue, the energy may on occasion damage the catheter body and effective re-entry may be prevented due to proximity of the wire tip to the catheter wall at the side-port. In other words, the tissue surrounding the wire at the side-port constrains the tip of the wire such that applied energy may not cut the vessel intima in the direction required for re-entry advancement of the wire.

The present inventors have discovered and reduced to practice a re-entry catheter having a geometry about the side-port which allows the tip of a medical device, for example, a wire such as an angled wire, to be positioned to exit the side-port in a desired direction and to avoid damaging a wall of the catheter when energy is delivered to the device. The side-port re-entry catheters have a configuration for the side-port wherein the catheter body wall has a first region at or adjacent to a distal end of the side-port being oriented in a first direction and second region adjacent to the first region being oriented in a second direction, wherein, typically, the second region defines at least part of the vestibule. Details of the unique geometry of the inventive embodiments, including configurations of a wall of the catheter body at or adjacent to a distal portion of the side-port, are described hereinbelow.

These embodiments provide several benefits and advantages, including but not limited to: 1) facilitating initial contact with tissue in the direction of desired advancement and establishing an initial trajectory such that the tip emerges from the side-port in the direction designed for re-entry such that, upon advancement, the wire will continue in that direction; 2) providing improved tissue contact for improving efficacy of energy delivery (particularly when using electrical energy; and 3) minimizing contact between a tip of the wire and the side-port wall (i.e. the surface of the catheter body which defines the side-port).

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The disclosed catheter is not limited to being used for re-entry procedures and may be used for other procedures. For example, the disclosed catheter may be used in a procedure involving bifurcated vessels. In one such example, a guide-wire could be advanced to a branch of a bifurcation. In the case of a bifurcation which is occluded, the disclosed catheter may be used to advance a cutting wire, sharp tipped or electrode tipped, into a branch of the occluded bifurcation.

As to be explained with respect to the drawings, components of typical embodiments of the invention are:

1) a side-port 13 defined by the wall of a catheter 8 (i.e. a side-port defined by a catheter body 9);

2) for embodiments for use with an angled wire, the sidewall of the catheter 8 in the vicinity of the side-port 13 is sufficiently thick to define a side-port of a depth adequate for an angled wire 19 to relax, at least in part, to its pre-set angled shaped, which positions the wire tip in contact with tissue adjacent the catheter in the direction required for re-entry, and ensures the tip is not in contact with the side-port edges (or other parts of the catheter body); in some (but not all) embodiments this is achieved by the catheter 8 having an off-center through-lumen 23 within catheter body 9 which provides greater wall thickness on the side-port side of the catheter relative to the side of the catheter opposite to the side-port, thereby reducing the total outer diameter of the catheter necessary to achieve the minimal necessary wall thickness (e.g. FIGS. 3b); and 3) the side-port 13 having a geometry which, when the wire 19 is positioned/directed to the side-port, positions the wire tip in contact with tissue in the direction required for re-entry, thereby limiting or preventing contact of the side-port wall 17 with the wire's tip (e.g. FIG. 4b).

Embodiments of catheter 8 may also be used with other devices, for example, a steerable wire. Embodiments of the catheter including a wire deflecting means may be used with a straight, deflectable wire. Catheter 8 may also be used with, for example, wires having a distal tip electrode configured for cutting tissue, or with suitably configured sharp tipped wires or devices, or with other suitable devices. For explanatory purposes, this disclosure typically describes the use of catheter with a wire.

FIG. 1 illustrates an embodiment of catheter 8 including a catheter body 9 defining a lumen 23, a side-port 13 in fluid communication with lumen 23, a proximal sleeve 31, a distal portion 22 of catheter body 9, a vestibule 11, a distal tip 25, an end opening 21 in fluid communication with lumen 23, and a marker 16. In this embodiment, lumen 23 is co-axial with catheter body 9 (i.e. lumen 23 is not off-center with respect to the catheter body). Details of vestibule 11 are described with respect to FIGS. 2, 3 and 4. Distal portion 22 is the portion of catheter body 9 distal of side-port 13. The marker 16 of FIG. 1 includes a marker band 16a and a marker backbone 16b. Marker band 16a is proximal of side-port 13, and marker backbone 16b is substantially parallel and opposite to side-port 13. Side-port 13 is typically elongate. In the embodiment of FIG. 1, the distal end of marker backbone 16b is slightly distal of side-port 13, and is substantially aligned with a distal end of vestibule 11. A wire braid layer 14, seen in the left side of the drawing, terminates proximally of side-port 13. The embodiment of FIG. 1 includes side-port 13 located in a recessed portion 10, unlike the embodiment of FIG. 4 (described below), which does not include the recessed portion. Recessed portion 10 comprises a portion of the catheter which is recessed from a surrounding portion of the catheter.

In the embodiment of FIG. 1, the inner diameter of catheter body 9 is about 0.040±0.004 inches (about 1.02±0.102 mm) at the distal end of wire braid layer 14 and is about 0.035±0.004 inches (0.89±0.102 mm) at the distal tip of the catheter (i.e. at end opening 21). The distance from the proximal end of marker band 16a to the distal tip of the catheter is about 0.587±0.294 inches (14.91±7.46 mm). The distance from the distal end of side-port 13 to the distal tip of the catheter is about 0.332±0.166 inches (8.43±4.21 mm).

Some embodiments of the catheter may be used with a 0.035 inch (0.89 mm) outer diameter (OD) guide-wire in a 6F introducer sheath. When the embodiment of catheter 8 of FIG. 1 is used with a 0.035 inch (0.89 mm) guide-wire, the inner diameter of 0.035±0.004 inches (0.89±0.102 mm) at end opening 21 will provide a close fit to the guide-wire and the relatively larger inner diameter of 0.040±0.004 inches (about 1.02±0.102 mm at the distal end of wire braid layer 14 will provide for trackability over the guide-wire.

Figure 2A:
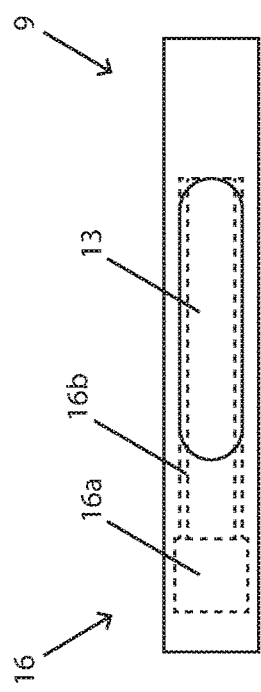
FIG. 2a to 2c are top views of portions of catheters illustrating different side-port embodiments.

FIG. 2a illustrates a portion of an embodiment of a catheter, including the side-port. Vestibule 11 is not shown in the illustration of FIG. 2a and is described with reference to FIGS. 3a and 3b hereinbelow. The embodiment of side-port 13 shown in FIG. 2a is elongate to allow an angled wire to have enough space to assume its relaxed position without hitting the surface defining the distal end of the side-port (side-port wall 17). The embodiment of side-port 13 of FIG. 2a has a straight side length of about 0.142±0.014 inches (3.61±0.36 mm) and end semi-circular portions each with a radius of about 0.020±0.002 inches (0.508±0.051 mm).

Figure 2B:
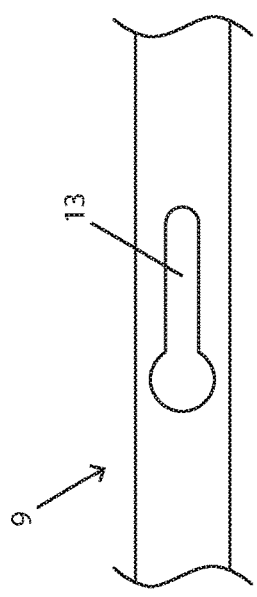
Figure 2C:
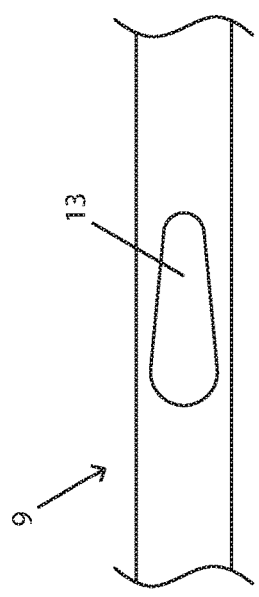

FIGS. 2b and 2c illustrate alternative embodiments of side-port 13. In FIG. 2b, side-port 13 is substantially keyhole-shaped. In FIG. 2c, side-port 13 has a substantially tapered oblong-shaped configuration having two elongate longitudinal sides that are substantially equal in length, and two rounded ends wherein one end is wider.

The embodiment of FIG. 2a also includes, in broken line, marker 16 which includes marker band 16a and marker backbone 16b. Marker 16 may be used in conjunction with medical imaging to visualize the location of side-port 13 and to help direct wire 19 towards a true lumen (or some other target). Typical embodiments of wire 19 also include imaging markers which may, in some embodiments, be alignable with marker 16. In some embodiments, marker 16 is radiopaque. Marker band 16a is proximal of side-port 13 and marker backbone 16b is substantially opposite to side-port 13 i.e. aligned at about 180° relative to the side-port. Unlike the embodiment of FIG. 1, the FIG. 2a embodiment includes the distal end of marker backbone 16b substantially aligning with the distal end of side-port 13 (in the embodiment of FIG. 1, the distal end of marker backbone 16b is slightly distal of side-port 13).

The length of marker 16 is about 0.256±0.026 inches (6.50±0.66 mm), the length of marker backbone 16b is about 0.216±0.022 inches (5.48±0.559 mm), the thickness of marker backbone 16b is about 0.010±0.01 inches (0.25±0.03 mm), the length of marker band 16a is about 0.040±0.004 inches (about 1.02±0.102 mm), the outer diameter of marker band 16a is about 0.050±0.005 inches (1.27±0.13 mm) and the inner diameter is about 0.044±0.004 inches (1.12±0.11 mm). The size and configuration of marker 16 may differ depending on the configuration of side-port 13, for example.

FIGS. 5a to 5c are cut away views showing different examples of markers. In the embodiment of FIG. 5a, a distal end 16c of marker 16 is located at a position approximately equivalent to a longitudinal mid-point of the side-port 13 for facilitating positioning of a device relative to the side-port. In the embodiment of FIG. 5b, a midpoint marker 26 is at a position approximately equivalent to a longitudinal mid-point of the side-port 13 for facilitating positioning of a device relative to the side-port. The example of FIG. 5c includes a flexible marker 27 which comprises a flexible radiopaque polymer and is distal of the side-port for facilitating positioning of a device relative to the side-port. In the example of FIG. 5c, flexible marker 27 is substantially about the same distance from side-port 13 as is marker band 16a to aid in visualizing the position of the side-port.

FIG. 3a is a perspective view of an embodiment of a catheter and FIG. 3b is a cut away view of the catheter of FIG. 3a. The embodiment of FIG. 3 includes a recessed portion 10 whereby side-port 13 is set back from the outer surface of catheter 8 defined by the outer diameter of catheter body 9, and a vestibule sidewall 12 which defines a vestibule 11. Vestibule 11 is adjacent to a distal region of the side-port 13. The vestibule 11 is operable for providing a gap (or clearance) between the catheter body 9 and a distal tip of a device (wire 19) positioned through the side-port. The thickness of the catheter body is greater at distal end 11a of the vestibule than at proximal end 11b of the vestibule. In other words, the vestibule is a gap in the outer portion of catheter body 9 that provides clearance for distal tip 32 of the wire to exit the catheter without contacting and possibly damaging catheter body 9. In the embodiment of FIGS. 3a and 3b, recessed portion 10 of catheter body 9 comprises a sloped surface distal of side-port 13; with FIG. 3b illustrating the sloped surface comprises a curved depression.

In FIGS. 3a and 3b, the first region 34 is comprised of the distal wall of side-port 13 and the second region 35 comprises a sloped surface defining a distal wall of the recessed portion.

The embodiment of FIGS. 3a and 3b further includes an off-center lumen 23 whereby catheter body 9 can provide sufficient sidewall thickness on the side-port side for the recessed portion 10. The catheter sidewall opposite the side-port is relatively thinner to reduce the total diameter of catheter 8. The sidewall of the catheter 8 in the vicinity of the side-port 13 is sufficiently for the side-port to have adequate depth for an angled wire 19 to relax, at least in part, to its pre-set angled shaped. The necessary side-port depth needed for this is dependent on the distance the tip of the angled wire is spaced apart from the central axis of the wire i.e. the lateral distance of the tip from the main shaft of the wire. The needed side-port depth determines the distance the lumen must be off center to accommodate an angled wire. For example, a wire having a tip with a relatively greater sideways displacement would require a relatively deeper side-port and a more off centered lumen.

The embodiment of side-port 13 of FIG. 3a has a substantially hourglass-shaped configuration. The wide proximal end of side-port 13 is easier to locate with the distal tip of wire 19 than a relatively narrower side-port; the narrow middle portion is operable to center the tip of an advancing wire 19 to aid in pointing the tip; and the wide distal portion of side-port 13 facilitates the distal tip of wire 19 exiting catheter 8. Alternative embodiments of catheter 8 comprise a side-port 13 that is substantially keyhole-shaped (e.g. FIG. 2b) or is a substantially tapered oblong-shaped configuration (e.g. FIG. 2c), with the proximal end of side-port 13 of such embodiments being relatively wider to facilitate locating the side-port with the tip of wire 19, and the distal end of side-port 13 being relatively narrower to assist in directing wire 19.

FIG. 4a is a top view of an alternative embodiment of a catheter including a side-port, and FIG. 4b is a cut away side view of the catheter of FIG. 4a. The side-port 13 of the embodiment of FIG. 4 is substantially not recessed, unlike the side-port of the embodiment of FIG. 3. The side-port wall 17 of FIG. 4b is substantially straight and at a 90° angle (perpendicular) to the longitudinal axis of the catheter, at both the proximal and distal ends of the side-port (as well as therebetween). Side-port 13 of FIG. 4 is similar in shape to the elongate capsule-shaped side-port of FIG. 2. Vestibule 11 of FIG. 4 may be described as a C-shaped or a semi-circular shaped cut in the catheter body 9 at the distal end of side-port 13.

As illustrated in FIG. 4b, the semi-circular shaped cut in the catheter body 9 removes a top portion of the distal end of side-port wall 17 while leaving a bottom portion of the wall intact. Vestibule 11 is at a distal region of the side-port 13. In the example of FIG. 4b, both the proximal wall and the distal wall of the side-port 13 are each defined by a wall of the catheter body 9.

In the embodiment of FIG. 4b, the first region 34 of the catheter body wall includes the distal wall of the side-port 13 and the second region 35 of the catheter body wall comprises a cut-away portion at an outer surface of the catheter body 9 (the vestibule) adjacent the distal wall of the side-port. The vestibule 11 is operable for providing a gap (or clearance) between the catheter body 9 and a distal tip of a device (wire 19) positioned through the side-port. The thickness of the catheter body is greater at a distal end 11a of the vestibule than at a proximal end 11b of the vestibule.

In some of the disclosed embodiments, vestibule 11 is a feature of catheter body 9 which is in communication with side-port 13 (e.g. FIGS. 3a and 3b), and in some other embodiments vestibule 11 is a feature of side-port 13 (e.g. FIG. 4b).

FIGS. 6a to 6g are cut away views showing the regions of the wall of catheter body 9 of different embodiments of side-port re-entry catheters. Each of the embodiments has a configuration wherein the wall of a catheter body 9 has a first region 34 at or adjacent to a distal end of the side-port 13 being oriented in a first direction and second region 35 adjacent to the first region 34 being oriented in a second direction, wherein the first and second regions cooperate to provide a longitudinal gap between a distal wall of the side-port and an outer surface of the catheter body. The division between the first and second regions is indicated in the drawings by a transition 33. Furthermore, in most of the embodiments, the second region 35 defines at least part of the vestibule 11.

Figure 6A:
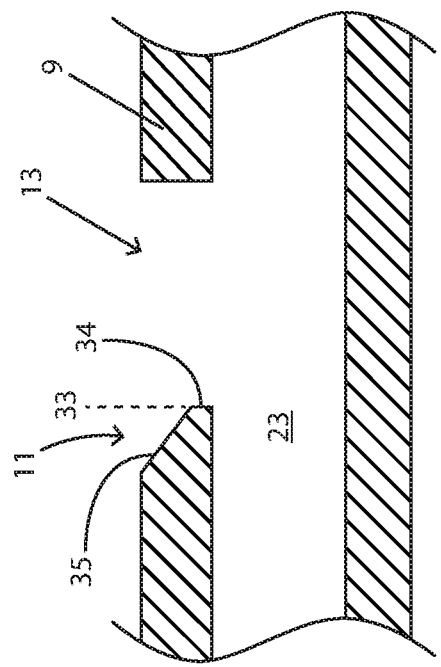
FIGS. 6a to 6g are cut away views showing the side-port region of different embodiments of catheters.

In the embodiment of FIG. 6a, first region 34 is perpendicular to a longitudinal axis of the catheter body 9, second region 35 is angled in a planar orientation relative to the first region and the second region 35 defines vestibule 11.

Figure 6B:
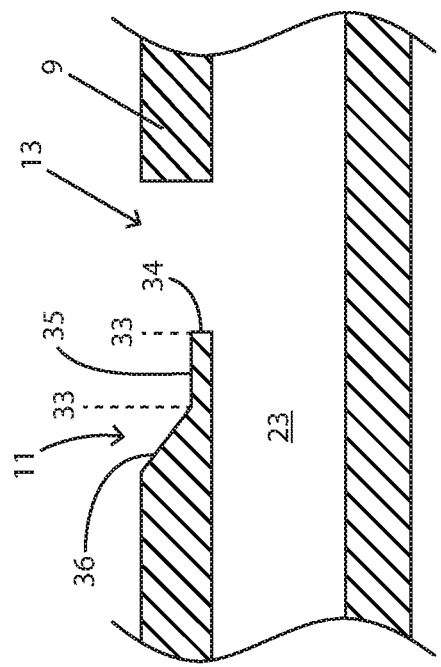

The example of FIG. 6b illustrates a first region 34 which is perpendicular to a longitudinal axis of the catheter body 9, a second region which 35 is angled in a planar orientation relative to the first region and is parallel to longitudinal axis of the catheter body 9. FIG. 6b further illustrates a third region 36 which is angled in a planar orientation relative to the second region and which defines the vestibule.

Figure 6C:
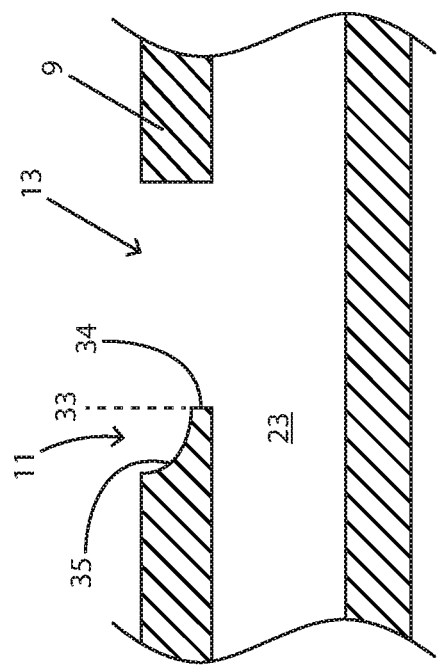

In the embodiment of FIG. 6c, first region 34 is perpendicular to a longitudinal axis of the catheter body 9, second region 35 is curved, and vestibule 11 is defined by second region 35. When the examples of FIGS. 6a, 6b, and 6c are in use, the first region 34 is operable to guide a device being advanced through the side-port in a direction different from the second direction of the second region 35.

Figure 6D:
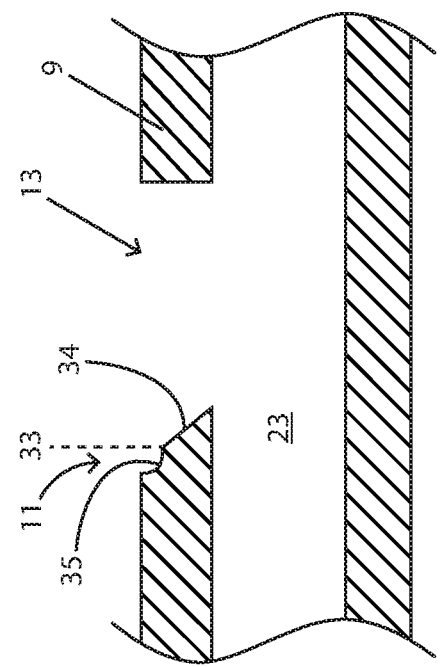

In the embodiment of FIG. 6d, the first region 34 is angled relative to a longitudinal axis of the catheter body 9 and the second region 35 defines a notch at the outer surface of the catheter body 9.

Figure 6G:
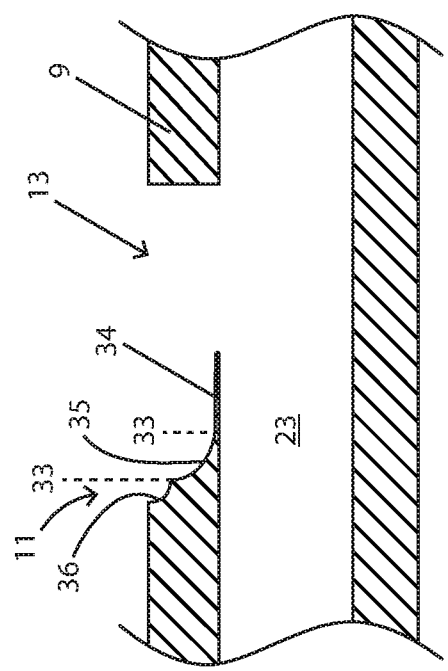
Figure 6E:
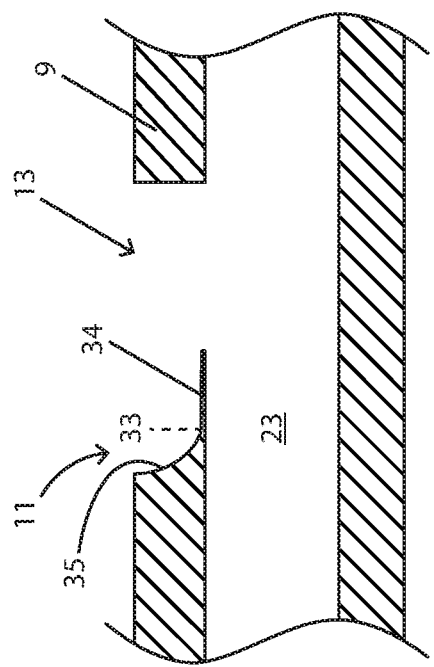

In the embodiment of FIG. 6e, the first region 34 is parallel to a longitudinal axis of the catheter body 9, the second region 35 is curved, and the second region defines vestibule 11.

Figure 6F:
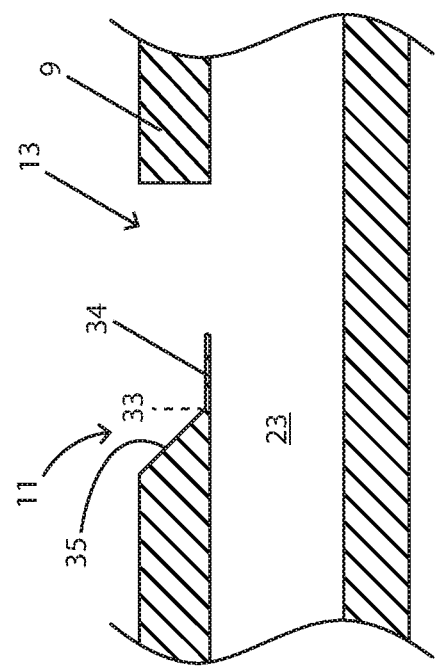

In the embodiment of FIG. 6f, the first region 34 is parallel to a longitudinal axis of the catheter body 9, the second region 35 is angled in a planar orientation relative to the first region, and the second region defines vestibule 11.

In the embodiment of FIG. 6g, the first region 34 is parallel to a longitudinal axis of the catheter body 9 and the second region 35 is curved, and the third region 36 defines a notch at the outer surface of the catheter body 9. In the example of FIG. 6g, the vestibule is defined by third region 36 at the end of second region 35. In the embodiments of FIGS. 6e, 6f, and 6g, the end of first region 34 closest to side-port 13 forms a point and is not considered to be a surface.

When an embodiments of 19 FIGS. 6e, 6f, and 6g is in use, the catheter is operable to have an angled wire 19 advanced along lumen 23 of with the distal tip 32 of the wire positioned within side-port 13, until until a side of the angled wire 19 abuts and is supported by a proximal end of the first region 34, whereby the proximal end of the first region is operable to function as a brace to direct the wire away from contacting the second region. In other words, when in use, the proximal end of the first region 34 is operable to function as a brace to direct a suitable device being advanced through side-port 13 away from contacting the second region 35.

With reference to the figures, an embodiment of a method of the present invention of using a medical device (e.g. a radiofrequency-based guide-wire) for re-entry into the true lumen of the vessel is described hereinbelow. The embodiment typically includes the steps of: (a) advancing a medical device, for example, an angled wire 19, through lumen 23 of catheter body 9 positioned within a wall of the vessel under imaging, and (b) locating side-port 13 (which is in fluid communication with the lumen) with the distal tip 32 of wire 19 wherein side-port 13 is elongate and a vestibule 11 is at or adjacent to a distal region of the side-port, and (c) positioning the wire 19 in the side-port 13 such that the distal tip 32 of wire 19 contacts a tissue (tissue not shown in FIG. 3) which abuts an outer surface of the catheter without distal tip 32 contacting a body of the catheter, such as is shown in the example of FIG. 3b. In FIG. 3b, wire 19 is bent which facilitates electrode 20 of wire 19 contacting tissue (not shown in drawings) that is pressing against the outer surface of catheter body 9 adjacent recessed portion 10 (and substantially covering or obstructing recessed portion 10) such that electrode 20 does not contact catheter body 9. Typically, both catheter body 9 and wire 19 include imaging markers to facilitate the step (b) of locating side-port 13 using the distal tip of wire 19 and step (c) of positioning the distal tip of wire 19. In typical embodiments of the method, wire 19 comprises an electrode 20, and the method further comprises a step (d) of delivering energy to the tissue through the electrode 20 to cut into the tissue. Typical embodiments of the method further comprise a step (e) of advancing the wire 19 into the tissue and into the true lumen of the vessel. In some embodiments of the method, wire 19 is advanced from the configuration of FIG. 3b, while simultaneously delivering energy, whereby electrode 20 cuts into tissue and wire 19 advances into the tissue. The energy may be, for example, radiofrequency or microwave electrical energy.

Some embodiments of the method comprise an alternative step (d) of advancing the angled wire (starting from the configuration of FIG. 3b) without delivering electrical energy, i.e. in the absence of energy delivery, such that electrode 20 slides along the constraining tissue substantially without puncturing the tissue until the side of wire 19 protrudes into the side-port 13, abuts an vestibule sidewall 12 associated with the side-port and vestibule sidewall 12 functions as a support or a brace for wire 19, at which time advancement of wire 19 is terminated, resulting in wire 19 being in a supported configuration. That the vestibule sidewall is associated with the side-port 13 should be understood to mean that a vestibule 11 may be a part of side-port, adjacent to the side-port or in communication with the side-port. In such embodiments of the method, wire 19 typically has an atraumatic tip whereby distal tip may slide along the tissue without damaging tissue before energy delivery. The supported configuration of wire 19 includes electrode 20 being in contact with the tissue but not in contact with vestibule sidewall 12 (or any part of catheter body 9). Such embodiments typically further include a step (e) of delivering energy to the tissue through electrode 20 (located at a distal tip of the angled wire 19) to cut into the tissue while avoiding/limiting damage to vestibule sidewall 12, and a step (f) of advancing the wire into the tissue.

A second embodiment of the method of the present invention of using a medical device (typically a wire such as an angled wire) for re-entry into a true lumen of a vessel comprises the steps of (a) advancing the medical device through a lumen of a catheter positioned within a wall of the vessel, (b) locating a side-port 13 in communication with the lumen 23 of the catheter with the medical device, (c) positioning the medical device in the side-port 13 such that a distal tip of the medical device is distanced from both catheter body 9 as well as a tissue of the vessel. The positioning of step (c) may occur, for example, when the medical device is a wire with distal bent portion which is long enough for a distal tip of the wire to fit into the side-port (and into recessed portion 10 for those embodiments of the catheter having the recessed portion) but the distal bent potion is not long enough for distal tip of the medical device to contact the tissue. This embodiment of the method includes the further steps (d) of further advancing the medical device along lumen 23 until a side of the medical device abuts and is supported by a vestibule sidewall 12 of a vestibule associated with the side-port 13 and the distal tip of the medical device is not in contact with the tissueto thereby define a first supported position, and (e) further advancing the medical device until the distal tip of the medical device contacts tissue while avoiding contact with the body of the catheter, to thereby define a second supported configuration. Typically, the second supported configuration includes an electrode 20 of the medical device being in contact with the tissue but not in contact vestibule sidewall 12 (or any part of catheter body 9). Typical embodiments include the electrode 20 being located at a distal tip of the angled medical device and the method further comprising a step (f) of delivering energy to the tissue whereby through the electrode to cut into the tissue. Typical embodiments further include a step (g) of advancing the medical device into the tissue.

Through the application of the above method, the distal tip electrode 20 of the medical device may be used to deliver energy to tissue without damaging side-port wall 17 or vestibule sidewall 12, thereby maintaining the integrity of catheter 8.

Despite the structural differences between the embodiments of FIGS. 3 and 4, the embodiment of FIG. 4 functions in a manner similar to that of FIG. 3 when used by one skilled in the art, and the above described method may be practiced using the embodiments of both FIGS. 3 and 4, and other embodiments disclosed herein.

Some alternative embodiments of the method include the use of a sharp-tipped mechanical wire rather than a wire with a distal tip electrode.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A catheter for delivering a medical device having a distal tip including an electrode when a layer of tissue is pressed against the catheter, the catheter comprising: a catheter body, the catheter body comprising a catheter body wall defining a lumen, and a side-port defined by a side of the catheter body wall in fluid communication with the lumen, the side-port being configured for delivering the medical device through the side-port when the layer of tissue is pressed against the side-port, the catheter having an outer surface and a longitudinal axis, the catheter body wall defining a vestibule and a side-port wall which is perpendicular to the longitudinal axis of the catheter, the side-port having a proximal end and a distal end, the side-port wall at the proximal end extending from the lumen to the outer surface of the catheter, the side-port wall at the distal end of the side-port extending perpendicularly from the lumen to the vestibule, the catheter body wall defining the vestibule as extending distally from the distal end of the side-port to the outer surface of the catheter wherein the side-port wall at the distal end of the side-port is configured to support a side of the medical device when the medical device is positioned through the side-port, wherein the vestibule defines a gap, whereby the distal tip of the medical device is positioned in the gap when the distal tip protrudes distally of the distal end of the side-port such that the distal tip of the medical device can contact the layer of tissue pressing against the side-port without contacting the catheter body wall.

2. The catheter of claim 1, wherein the vestibule is C-shaped and has a proximal end which is closer to the lumen than a distal end of the vestibule.

3. The catheter of claim 1, wherein when the catheter is in use, the distal tip of the medical device positioned through the side-port and located within the vestibule is spaced apart from the catheter body wall to avoid damaging the catheter body wall when energy is delivered through the electrode.

4. The catheter of claim 1 for use with the medical device wherein the medical device is an angled wire, wherein the catheter body wall defining the lumen comprises a single lumen, the single lumen is in fluid communication with a distal end opening of the catheter, the single lumen is off-center within the catheter body, and a wall thickness of the catheter body wall is greater on the side of the catheter body wall defining the side-port relative to an opposite side of the catheter body wherein the side-port has an elongate shape configured to allow the angled wire to have enough space to assume its relaxed position without hitting the distal end of the side-port.

5. The catheter of claim 1, wherein the side-port is substantially elongate.

6. The catheter of claim 5, wherein the side-port has a relatively wider portion and a relatively narrower portion and is keyhole-shaped.

7. The catheter of claim 6, wherein the relatively wider portion is proximal of the relatively narrower portion.

8. The catheter of claim 1, wherein the catheter body wall defining the lumen defines a single lumen of constant diameter and a forward facing distal end opening.

9. A kit comprising the catheter of claim 1 and at least one angled wire.

10. A method of using a catheter and an angled wire for re-entry a true lumen of a vessel wherein the catheter comprises a catheter body, the catheter body having, a catheter body wall defining a lumen, and a side-port defined by a side of the catheter body wall in fluid communication with the lumen, the catheter having an outer surface and a longitudinal axis, the catheter body wall defining a vestibule and a side-port wall winch is perpendicular to the longitudinal axis of the catheter, the side-port having a proximal end and a distal end, the side-port wail at the proximal end extending from the lumen to the outer surface of the catheter, the side-port wall at the distal end of the side-port extending perpendicularly from the lumen to the vestibule, the catheter body wall defining the vestibule as extending distally from the distal end of the side-port to the outer surface of the catheter, the method comprising the steps of:
   (a) advancing the angled wire through the lumen of the catheter which has a distal end opening and which is positioned sub-intimally within a wall 3 f the vessel such that a layer of tissue of the vessel contacts the outer surface of the catheter adjacent and surrounding the side-port whereby the layer of tissue covers the side-port and wherein the lumen is in fluid communication with the side-port and the distal end opening:
   (b) positioning a distal tip of the angled wire through the side-port which has a longitudinally elongate opening such that the distal tip contacts the layer of tissue which covers the longitudinally elongate opening of the side-port without contacting a side of the distal end of the side-port, and
   (c) wherein the side of the distal end of the side-port has the vestibule cut into an outer portion of it which is adjacent the outer surface of the body of the catheter to provide for advancing the angled wire through the side-port such that the distal tip of the angled wire slides along the layer of tissue without puncturing the layer of tissue until a side of the angled device is supported by an inner portion of the distal end of the side-port.

11. The method of claim 10, wherein the angled wire comprises an electrode at the distal tip thereof and wherein the method further comprises a step (d) of delivering energy to the layer of tissue through the electrode to cut the layer of tissue.

12. The method of claim 11, wherein the energy is selected from the group consisting of radiofrequency electrical energy and microwave electrical energy.

13. A method of using a catheter and an angled wire for re-entry into a true lumen of a vessel wherein the catheter comprises a catheter body, the catheter body having a catheter body wall defining a lumen, and a side-port defined by a side of the catheter body wall in fluid communication with the lumen, the catheter having an outer surface and a longitudinal axis. the catheter body wall defining a vestibule and a side-port wall which is perpendicular to the longitudinal axis of the catheter, the side-port having a proximal end and a distal end, the side-port w all at the proximal end extending from the lumen to the outer surface of the catheter, the side-port wall at the distal end of the side-port extending perpendicularly from the lumen to the vestibule, the catheter body wall defining the vestibule as extending distally from the distal end of the side-port to the outer surface of the catheter, the method comprising the steps of:
   (a) advancing the angled wire through the lumen of the catheter which has a distal end opening and which is positioned sub-intimally within a wall of the vessel such that a layer of tissue of the vessel contacts the outer surface of the catheter body adjacent the side-port whereby the layer of tissue covers the side-port and wherein the lumen is in fluid communication with the side-port and the distal end opening;
   (b) positioning the angled wire through the side-port which has a longitudinally elongate opening such that a distal tip of the angled wire is spaced apart from both a side of the distal end of the side-port as well as the layer of tissue which is covering the longitudinally elongate opening of the side-port, and
   (c) wherein the side of the distal end of the side-port has the vestibule cut into an outer portion of it which is adjacent the outer surface of the body of the catheter, such that further advancing the angled wire causes a side of the angled wire to abut and be supported by an inner portion of the distal end of the side-port which is adjacent the lumen while avoiding contact with the layer of tissue.

14. The method of claim 13, further comprising a step (d) of further advancing the angled wire until the distal tip of the angled wire contacts the layer of tissue while avoiding contact with the distal end of the side-port.

15. The method of claim 14, wherein the angled wire comprises an electrode located at the distal tip thereof and wherein the method further comprises a step (e) of delivering an energy to the layer of tissue through the electrode to cut the layer of tissue.

16. The method of claim 15, wherein the energy is selected from the group consisting of radiofrequency electrical energy and microwave electrical energy.

17. The method of claim 13, wherein the catheter comprises a radiopaque marker for positioning the angle wire relative to the side-port.

* * * * *